United States Patent
Hsu et al.

(10) Patent No.: US 11,011,275 B2
(45) Date of Patent: May 18, 2021

(54) SYSTEM AND METHOD FOR DIAGNOSING GASTROINTESTINAL NEOPLASM

(71) Applicant: AI.SKOPY, INC., San Jose, CA (US)

(72) Inventors: Chih-Chung Hsu, Taichung (TW); Tsung-Chun Lee, New Taipei (TW)

(73) Assignee: AI.SKOPY, INC., San Jose, CA (US)

( * ) Notice: Subject to any disclaimer, the term of this patent is extended or adjusted under 35 U.S.C. 154(b) by 60 days.

(21) Appl. No.: 16/273,016

(22) Filed: Feb. 11, 2019

(65) Prior Publication Data

US 2019/0252073 A1     Aug. 15, 2019

Related U.S. Application Data

(60) Provisional application No. 62/629,600, filed on Feb. 12, 2018.

(51) Int. Cl.
    *G16H 50/20*     (2018.01)
    *G16H 30/40*     (2018.01)
    (Continued)

(52) U.S. Cl.
    CPC ........... *G16H 50/20* (2018.01); *G06N 3/0454* (2013.01); *G06N 3/0472* (2013.01); *G06N 3/08* (2013.01);
    (Continued)

(58) Field of Classification Search
    CPC .......... G16H 50/20; G16H 30/40; G06N 3/08; G06N 3/0454; G06N 3/0472;
    (Continued)

(56) References Cited

U.S. PATENT DOCUMENTS

| | | | |
|---|---|---|---|
| 2007/0099219 A1* | 5/2007 | Teverovskiy | G16H 50/50 435/6.16 |
| 2013/0182931 A1* | 7/2013 | Fan | G06T 7/143 382/131 |

(Continued)

FOREIGN PATENT DOCUMENTS

| | | | | |
|---|---|---|---|---|
| CN | 109242844 | * | 1/2019 | G06T 7/00 |

OTHER PUBLICATIONS

Anonymous: "Pentx i-Scan™ Functionality, Application, and Technical Analysis", Dec. 30, 2013 (Dec. 30, 2013), pp. 1-8, XP055581667; Retrieved from the Internet: URL: <https://www.pentaxmedical.com/pentax/download/fstore/uploadFiles/Pdfs/Case%20Studies/AMER_GI_CS_MK-412-Rev.-A_i-Scan-White-Paper%20(1)_3.pdf [retrieved on Apr. 16, 2019].

(Continued)

*Primary Examiner* — Jerome Grant, II
(74) *Attorney, Agent, or Firm* — Knobbe, Martens, Olson and Bear, LLP

(57) ABSTRACT

A system and method of diagnosing gastrointestinal neoplasm or pathologies in an endoscopy system including an endoscopy system display for displaying an image enhanced endoscopy (IEE) image. The method includes randomly generating training image samples with or without cancer region(s) by an adversarial network (AN) including collecting endoscopic training images (T1) and automatically generating a realistic IEE image as a new training image sample (T2) using a generator network in the AN from a generated segmentation map; using a prediction network (L1PN) to learn a level 1 prediction result being a cancerous probability of an IEE image from the collected T1 and T2; using a prediction network (L2PN) to learn a level 2 prediction result being detected cancerous region(s) of an IEE image; and predicting the level 1 result and the level 2 result for an (Continued)

IEE image using the L1PN and the L2PN and without using the AN.

15 Claims, 12 Drawing Sheets
(12 of 12 Drawing Sheet(s) Filed in Color)

(51) Int. Cl.
| | |
|---|---|
| *G06T 7/00* | (2017.01) |
| *G06N 3/08* | (2006.01) |
| *G06N 3/04* | (2006.01) |
| *G09B 23/28* | (2006.01) |
| *A61B 1/273* | (2006.01) |
| *A61B 1/00* | (2006.01) |

(52) U.S. Cl.
CPC .......... *G06T 7/0012* (2013.01); *G09B 23/285* (2013.01); *G16H 30/40* (2018.01); *A61B 1/00009* (2013.01); *A61B 1/2736* (2013.01); *G06T 2207/10068* (2013.01); *G06T 2207/30028* (2013.01)

(58) Field of Classification Search
CPC ................ G09B 23/285; G06T 7/0012; G06T 2207/30028; G06T 2207/10068; A61B 1/2736; A61B 1/0009
USPC ......................................................... 382/128
See application file for complete search history.

(56) References Cited

U.S. PATENT DOCUMENTS

| | | | | |
|---|---|---|---|---|
| 2016/0005183 | A1* | 1/2016 | Thiagarajan | G06T 7/0012 382/131 |
| 2018/0242906 | A1* | 8/2018 | Madabhushi | A61B 5/4839 |
| 2018/0276825 | A1* | 9/2018 | Dai | A61B 5/7267 |
| 2019/0026897 | A1* | 1/2019 | Wu | G06T 7/11 |
| 2019/0042826 | A1* | 2/2019 | Chang | G06T 7/11 |
| 2019/0156476 | A1* | 5/2019 | Yoshida | G06K 9/6269 |

OTHER PUBLICATIONS

International Search Report and Written Opinion dated Apr. 30, 2019 for PCT/US2019/017668, in 12 pages.
Goodfellow, I., Pouget-Abadie, J., Mirza, M., Xu, B., Warde-Farley, D., Ozair, S., Courville, A., and Bengio, Y. (2014), Generative adversarial nets, In Advances in neural information processing systems (pp. 2672-2680).
He, K., Gkioxari, G., Dollár, P., & Girshick, R. (2017), Mask R-CNN, In Proceedings of the IEEE international conference on computer vision (pp. 2961-2969).
Huang, G., Liu, Z., Van Der Maaten, L., & Weinberger, K. Q. (2017), Densely connected convolutional networks, In Proceedings of the IEEE conference on computer vision and pattern recognition (pp. 4700-4708).
Kingma, D. P., & BA, J (2015), Adam: A method for stochastic optimization, International Conference on Learning Representations, (pp. 1-15).
Long, J., Shelhamer, E., & Darrell, T. (2015), Fully convolutional networks for semantic segmentation, In Proceedings of the IEEE conference on computer vision and pattern recognition (pp. 3431-3440).
Shrivastava, A., Pfister, T., Tuzel, O., Susskind, J., Wang, W., & Webb, R. (2017), Learning from simulated and unsupervised images through adversarial training, In Proceedings of the IEEE Conference on Computer Vision and Pattern Recognition (pp. 2107-2116).

* cited by examiner

SYSTEM AND METHOD FOR DIAGNOSING GASTROINTESTINAL NEOPLASM

RELATED APPLICATIONS

This application claims priority to U.S. Application No. 62/629,600, filed on Feb. 12, 2018, which is incorporated herein by reference in its entirety.

BACKGROUND

Field

The disclosed technology relates to endoscopy and, more particularly, to early diagnosis and detection of early stage gastric cancers (and other GI cancers as well) by endoscopy.

Description of the Related Technology

The demand for diagnosing gastrointestinal (GI) cancers by endoscopy is increasing, but only a limited number of experienced endoscopy doctors can detect and not miss lesions (especially early stage cancers). Hence, the computer-aided diagnosis, through the advancement of deep learning to significantly increase the accuracy/sensitivity/specificity performance (up to 95% level) than traditional image feature analysis methods (in some studies at the level of about 50-70%), can facilitate assisting doctors practicing endoscopy to diagnose and detect early stage GI cancers.

Conventional image analysis methods to diagnose early stage gastric cancers using pre-defined image features have been found to only perform in a range of about 50-70% for accuracy, sensitivity and specificity.

SUMMARY OF CERTAIN INVENTIVE ASPECTS

The system and method of the technology each have several aspects, no single one of which is solely responsible for its desirable attributes. Without limiting the scope of this invention, some aspects will now be briefly discussed.

In one aspect of the development, there is a method of diagnosing gastrointestinal neoplasm or pathologies in an endoscopy system including an endoscopy system display for the display of an image enhanced endoscopy (IEE) image, the method comprising randomly generating training image samples with or without cancer region(s) by an adversarial network (AN), comprising collecting endoscopic training images (T1); partitioning the training images into training normal blocks and training cancerous blocks according to a corresponding segmentation map (S1); learning to automatically generate cancerous blocks using a cancerous generative adversarial network (CGAN) from the training cancerous blocks; learning to automatically generate normal IEE image blocks using a normal generative adversarial network (NGAN) from the training normal blocks; randomly generating segmentation maps (S2) comprising a black and white image based on the automatically generated cancerous blocks and the automatically generated normal IEE image blocks, wherein any white pixels indicate a cancerous region, and wherein the segmentation map can be black pixels only, which is indicative of no cancer; learning to automatically generate a realistic IEE image as a new training image sample (T2) using a generator network in the AN from the generated segmentation map; using a level 1 prediction network (L1PN) to learn a level 1 prediction result being a cancerous probability of an IEE image from the collected T1 and T2, wherein T2 is generated by the AN; using a level 2 prediction network (L2PN) to learn a level 2 prediction result being detected cancerous region(s) of an IEE image from the collected T1 and T2, wherein T2 is generated by the AN; and predicting the level 1 result and the level 2 result for an IEE image using the L1PN and the L2PN and without using the AN.

The IEE images may include at least one of magnified narrow-band imaging, endocytomicroscopy, i-SCAN, flexible spectral imaging color enhancement, blue laser imaging, and bright laser imaging. The segmentation map (S1) may comprise a ground truth. The ground truth may be labeled by a physician. The method may additionally comprise generating additional training images based on the collected endoscopic training images, the generating comprising: rotating or flipping a collected endoscopic training image to create one or more augmented training images; providing a guided segmentation map having a resolution greater than the collected endoscopic training images; randomly cropping the guided segmentation map to obtain a sub-map having a resolution equal to the resolution of the collected endoscopic training images; and multiplying the sub-map with each of the augmented training images so as to produce additional training images. The detected cancerous region(s) of the level 2 prediction result may be at a pixel level of resolution.

In another aspect of the development there is a system for diagnosing gastrointestinal neoplasm or pathologies in an endoscopy system including an endoscopy system display for the display of an image enhanced endoscopy (IEE) image, the system comprising means for randomly generating training image samples with or without cancer region(s) by an adversarial network (AN), comprising means for collecting endoscopic training images (T1); means for partitioning the training images into training normal blocks and training cancerous blocks according to a corresponding segmentation map (S1); means for learning to automatically generate cancerous blocks using a cancerous generative adversarial network (CGAN) from the training cancerous blocks; means for learning to automatically generate normal IEE image blocks using a normal generative adversarial network (NGAN) from the training normal blocks; means for randomly generating segmentation maps (S2) comprising a black and white image based on the automatically generated cancerous blocks and the automatically generated normal IEE image blocks, wherein any white pixels indicate a cancerous region, and wherein the segmentation map can be black pixels only, which is indicative of no cancer; means for learning to automatically generate a realistic IEE image as a new training image sample (T2) using a generator network in the AN from the generated segmentation map; means for using a level 1 prediction network (L1PN) to learn a level 1 prediction result being a cancerous probability of an IEE image from the collected T1 and T2, wherein T2 is generated by the AN; means for using a level 2 prediction network (L2PN) to learn a level 2 prediction result being detected cancerous region(s) of an IEE image from the collected T1 and T2, wherein T2 is generated by the AN; and means for predicting the level 1 result and the level 2 result for an IEE image using the L1PN and the L2PN and without using the AN.

The IEE images may include at least one of magnified narrow-band imaging, endocytomicroscopy, i-SCAN, flexible spectral imaging color enhancement, blue laser imaging, and bright laser imaging. The segmentation map (S1) may comprise a ground truth. The ground truth may be labeled by a physician. The system may additionally comprise means for generating additional training images based on the collected endoscopic training images, the means for generating comprising: means for rotating or flipping a collected endoscopic training image to create one or more augmented training images; means for providing a guided segmentation map having a resolution greater than the collected endoscopic training images; means for randomly cropping the guided segmentation map to obtain a sub-map having a resolution equal to the resolution of the collected endoscopic training images; and means for multiplying the sub-map with each of the augmented training images so as to produce additional training images. The detected cancerous region(s) of the level 2 prediction result may be at a pixel level of resolution.

In another aspect of the development there is a method of randomly generating training image samples with or without cancer region(s) by an adversarial network (AN), in an endoscopy system for diagnosing gastrointestinal neoplasm or pathologies including an endoscopy system display for the display of an image enhanced endoscopy (IEE) image, the method comprising providing endoscopic training images (T1), partitioning the training images into training normal blocks and training cancerous blocks according to a corresponding segmentation map (S1), learning to automatically generate cancerous image blocks using a cancerous generative adversarial network (CGAN) from the training cancerous blocks, learning to automatically generate normal image blocks using a normal generative adversarial network (NGAN) from the training normal blocks, randomly generating a segmentation map (S2) comprising an image based on the automatically generated cancerous image blocks and the automatically generated normal image blocks, and learning to automatically generate a realistic IEE image as a new training image sample (T2) using a generator network in the AN from the generated segmentation map.

Any white pixels may indicate a cancerous region in the segmentation map, and wherein the segmentation map may be black pixels only, which is indicative of no cancer.

In another aspect of the development there is a method of diagnosing gastrointestinal neoplasm or pathologies in an endoscopy system including an endoscopy system display for the display of an image enhanced endoscopy (IEE) image, the method comprising using a level 1 prediction network (L1PN) comprising feature extraction followed by segmentation to learn a level 1 prediction result being a cancerous probability of an IEE image from collected training images, using a level 2 prediction network (L2PN) comprising feature extraction feeding a predictive network to learn a level 2 prediction result being detected cancerous region(s) of an IEE image from the collected training images, and predicting the level 1 result and the level 2 result for an IEE image using the L1PN and the L2PN.

In yet another aspect of the development there is a system for processing radiological images, comprising a feature extraction network configured to receive a radiological image to be processed, a segmentation network configured to receive output of the feature extraction network and generate cancerous localization results, and a predictive network configured to receive output of the feature extraction network and generate cancerous detection results.

BRIEF DESCRIPTION OF THE DRAWINGS

This application contains at least one drawing executed in color. Copies of this patent with color drawing(s) will be provided by the Office upon request and payment of the necessary fee.

DETAILED DESCRIPTION OF CERTAIN ILLUSTRATIVE EMBODIMENTS

Figure 1:
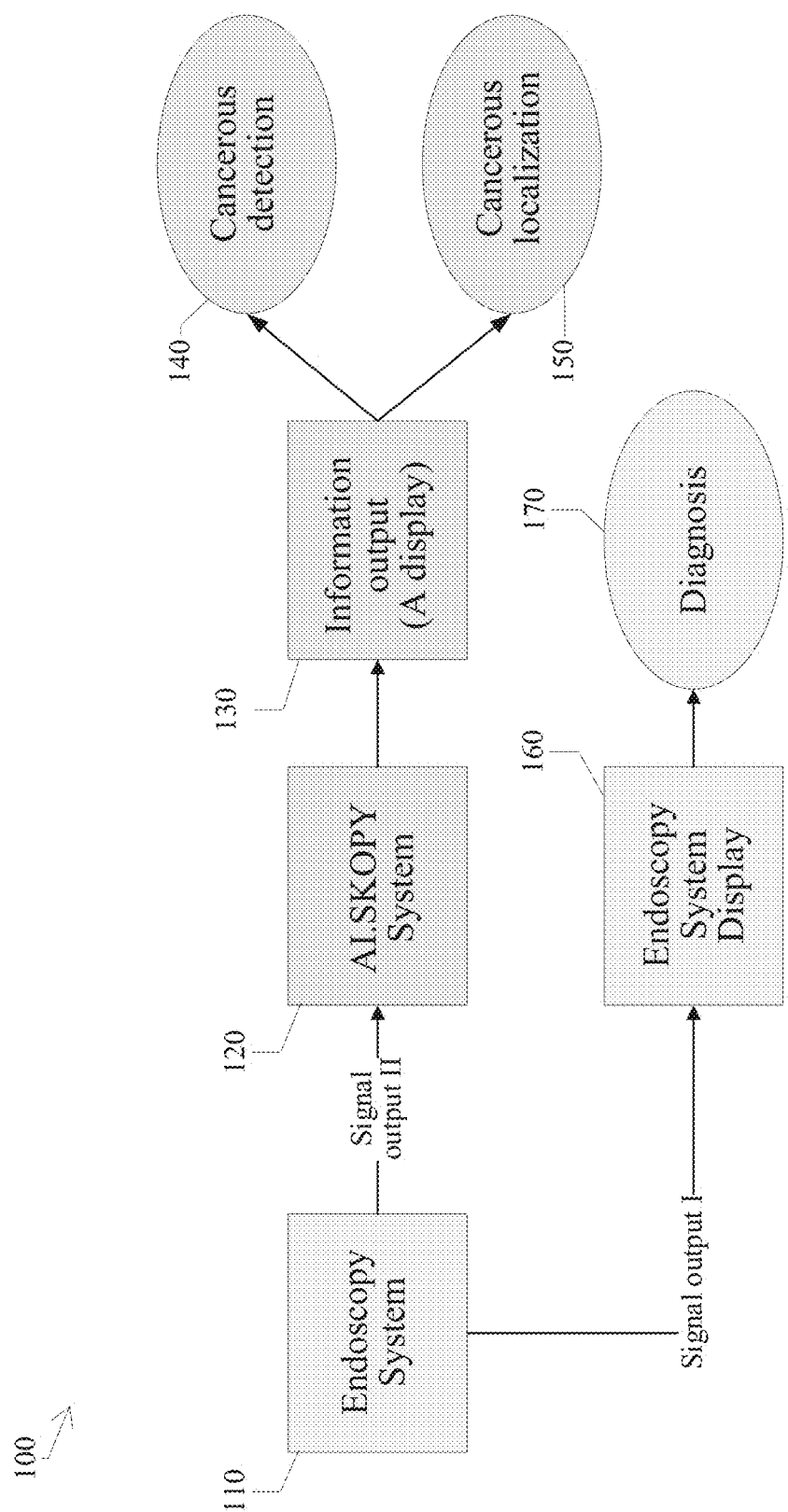
FIG. 1 is a block diagram showing an overall framework of a computer-aided diagnosis system which includes an artificial intelligence component for image recognition known as the AI.SKOPY system.

The following detailed description of certain illustrative embodiments presents various descriptions of specific embodiments of the invention. However, the invention can be embodied in a multitude of different ways.

The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Models representing data relationships and patterns, such as functions, algorithms, systems, and the like, may accept input (sometimes referred to as an input vector), and produce output (sometimes referred to as an output vector) that corresponds to the input in some way. For example, a model may be implemented as an artificial neural network (NN). Artificial neural networks are artificial in the sense that they are computational entities, analogous to biological neural networks in animals, but implemented by computing devices. Output in NN-based models is obtained by doing a forward pass. The forward pass involves multiplying large NN weight matrices, representing the parameters of the model, by vectors corresponding to input feature vectors or hidden intermediate representations. In recognition systems, such as systems designed to recognize speech, handwriting, faces, and the like, NN-based models may generate probability scores via the forward pass. The probability scores may indicate the probability that the input corresponds to a particular label, class, or the like.

The parameters of a NN can be set in a process referred to as training. For example, a NN-based model can be trained using training data that includes input data and the correct or preferred output of the model for the corresponding input data. Sets of individual input vectors may be processed at the same time by using an input matrix instead of a single input vector. The NN can repeatedly process the input data, and the parameters (e.g., the weight matrices) of the NN can be modified until the model produces (or converges on) the correct or preferred output. The modification of weight values may be performed through a process referred to as back propagation. Back propagation includes determining the difference between the expected model output and the obtained model output, and then determining how to modify the values of some or all parameters of the model to reduce the difference between the expected model output and the obtained model output.

Generally described, artificial neural networks, including but not limited to deep neural networks, have multiple layers of nodes. Illustratively, a NN may include an input layer, and output layer, and any number of intermediate or hidden layers between the input and output layers. The individual layers may include any number of separate nodes. Nodes of adjacent layers may be connected to each other, and each connection between the various nodes of adjacent layers may be associated with a respective weight. Conceptually, a node may be thought of as a computational unit that computes an output value as a function of a plurality of different input values. The input values may include the output of nodes in a previous layer, multiplied by weights associated with connections between the nodes in the previous layer and the current node. When a NN processes input data in the form of a matrix of input vectors (e.g., a batch of training data input vectors), the NN may perform a forward pass to generate a matrix of output vectors. The input vectors may each include n separate data elements or dimensions, corresponding to the n nodes of the NN input layer (where n is some positive integer). Each data element may be a value, such as a floating point number or integer. The forward pass includes multiplying the matrix of input vectors by a matrix representing the weights associated with connections between the nodes of the input layer and nodes of the next layer, and applying an activation function to the results. The process is then repeated for each subsequent NN layer.

By using end-to-end deep learning methodology, the performance of diagnosis of early stage gastric cancers and detection of cancerous areas made a leapfrog improvement, in at least one study, to the range of 85-95%.

In general, deep learning requires a large-scale training set to reach good and stable performance on various tasks. However, there are not enough training samples in several applications such as medical imaging or the imaging captured from new devices. This development provides an effective and efficient deep learning framework that can be used on small-scale training samples for specified object localization and detection.

Exemplary use cases for the development include gastrointestinal cancer detection and localization in or supplementary to an endoscopy system. A system can focus on diagnosis and detection of early gastric cancers on image enhanced endoscopy (IEE) images (e.g., magnified narrow-band imaging endoscopy), but the same working model and processes can be applied to other gastrointestinal pathologies/cancers as well, e.g., early esophageal cancers, Barrett's esophagus, and colorectal polyps/cancers.

Other additional clinical applications of this development include monitoring and surveillance of intestinal inflammation (e.g., colitis) in inflammatory bowel disease (Crohn's disease, ulcerative colitis).

The development is not restricted to the type of IEE and is applicable to IEE, which include magnified narrow-band imaging, endocytomicroscopy, i-SCAN, flexible spectral imaging color enhancement, blue laser imaging, and bright laser imaging. Magnified narrow-band imaging is herein utilized as an exemplary use case.

Two high level capabilities are as follows:
1. A high performance computer-aided diagnosis system provides cancer region localization and detection.
2. An effective and efficient deep learning framework permits use of small-scale sample data sets for training.

The framework uses a convolutional neural network (CNN) and a generative adversarial network (GAN). A goal of the system is object region detection and localization or semantic segmentation. Existing techniques are provided in the following list. Each of these three documents is incorporated by reference in its entirety.
1. He, Kaiming, et al. "Mask r-cnn." arXiv preprint arXiv:1703.06870 (2017).
2. Long, Jonathan, Evan Shelhamer, and Trevor Darrell. "Fully convolutional networks for semantic segmentation." Proceedings of the IEEE Conference on Computer Vision and Pattern Recognition (2015).
3. Shrivastava, Ashish, et al. "Learning from simulated and unsupervised images through adversarial training." arXiv preprint arXiv:1612.07828 (2016).

In certain embodiments, the image augmentation technique of this development contains three GANs and can generate the discriminative images of the specified identity controlled by a controller factor. Moreover, a M-NBI image can be generated with the specified cancerous region. Conventional methods cannot generate the image with the specified cancerous region.

A new CNN architecture has been designed including:
All 3*3 kernel: Traditional CNN uses 7*7 or even larger kernel in the first 1-3 layers to reduce computational complexity. However, that size would reduce the spatial resolution here and the feature in M-NBI is very insignificant so that a smaller kernel size is utilized to keep the spatial resolution.
No pooling is used, but strided convolution is used: Pooling would destroy the spatial relation and in M-NBI images, the relation between pixels is important, which is why pooling is not used.
A number of feature extractor layers (e.g., six); a number of segmentation layers (e.g., four); and a number of predictive layers (e.g., four): The number of these layers in the new CNN architecture are empirically determined according to several experiments. In certain embodiments, these values provide the best trade-off between computational complexity and performance.

Advantages of the development include:
Only a small-scale data set of samples is needed for training
Real-time computer-aid diagnosis system for endoscopy
Fast and accurate cancer region localization
A fast and effective CNN for cancer location detection in endoscopy system
A real-time computer-aid endoscopy diagnosis system
Content-aware data augmentation of a training phase of the level 2 prediction network from a small-scale data set A M-NBI images synthesis technique that can be used to generate the synthetic—NBI images with/without cancer regions.

New features of this development are as follows:
1. The convolutional neuronal network structures are new in this development. The unique CNN structures (FIGS. 2-3 and 5-7 are designed to generate Level-1 output (whole image diagnosis of cancer or not) and Level-2 output (pixel-level cancerous region indication).
2. Automatically generation of realistic training M-NBI images with/without cancerous regions.

An Embodiment of the Set of Steps and Components to Perform the Process
1. Randomly generating training images with or without cancer region(s) by adversarial network (AN).
    1.1. Collecting training images (T1)
    1.2. Partition images into normal blocks and cancerous blocks according to the corresponding segmentation map.
    1.3. Learning to automatically generate cancerous blocks using a cancerous generative adversarial network (CGAN) from training cancerous blocks.
    1.4. Learning to automatically generate normal magnified narrow band imaging (M-NBI) image blocks using a normal generative adversarial network (NGAN) from training normal blocks.
    1.5. Randomly generating a segmentation map (black and white image only where the white region means cancerous region). The segmentation map can be black pixels only, which means there is no cancer.
    1.6. According to 1.5, the black region will be filled from the result in 1.4 whereas the white region will be filled from the result in 1.3.
    1.7. Learning to automatically generate a realistic M-NBI image using generator network in AN from the results in 1.6. The generated results can be regarded as a new training sample (T2).
2. Use L1PN to learn the level 1 prediction result (cancerous probability of an M-NBI image) from collected T1 and T2, where T2 is generated by AN.
3. Use L2PN to learn the level 2 prediction result (detecting cancerous regions of an M-NBI image) from collected T1 and T2, where T2 is generated by AN.
4. After training process has done, use L1PN and L2PN to predict the L1 and L2 results for an M-NBI image. In this step, AN is no longer needed.

The three top-level components of the system operating on training images to produce a magnified narrow-band imaging (M-NBI) result are as follows:
A. Adversarial network (AN)—This is used to train L1PN and L2PN and not used in testing phase. Testing phase=generating the diagnosis result of an M-NBI image.
B. Level 1 prediction network (L1PN) of CNN
C. Level 2 prediction network (L2PN) of CNN The following are the second level components of the AN, L1PN and L2PN:
A. Adversarial network (AN)
    1. Training images
    2. Cancerous GAN (CGAN)
    3. Normal GAN (NGAN)
    4. Generator network
    5. Discriminator network
    6. Final GAN
    7. Synthesized images
B. Level 1 prediction network (L1PN)
    1. Loss function for L1PN
    2. Feature extractor
    3. Level one prediction
C. Level 2 prediction network (L2PN)
    1. Loss function for L2PN
    2. Feature extractor
    3. Segmentation
    4. Level two segmentation map The level one prediction and level two segmentation map are used to generate the M-NBI image. As described in the above set of steps, realistic M-NBI images are generated using AN only. While the AN has trained, AN can be used to synthesize any normal M-NBI image and cancerous N-NBI image. This can be used to augment the size of the training set. When there is a large-scale training set, an effective L1PN and L2PN can be trained. Finally, The L1PN and L2PN can be used to predict the cancerous probability and its location for an M-NBI image.

A Fully Connected (FC) layer and Softmax function can be placed at the end of L1PN. These are common strategies to make CNN work well.

FIG. 1 shows the overall framework of the exemplary computer-aided diagnosis system 100. A component artificial intelligence system 120, referred to as an AI.SKOPY system, can be applied to receive image input any suitable existing endoscopy system 110 with any video signal output (e.g., RGB or YCbCr). A traditional endoscopy system will show the endoscopic image on a display monitor 160. Doctors then can view the endoscopic image and make a diagnosis 170 as to whether the endoscopic image is cancerous or not, based upon viewing the images on block 6 endoscopy system display. The AI.SKOPY system 120 can receive an endoscopy image signal (still frame images or video) and analyze the image signal (still frame images or video) content, then generate the output result on a display 130 with two levels of information: 1) cancerous detection 140 and its probability and 2) cancerous region localization 150 (if any).

Training Phase of L1PN/L2PN

Figure 2:
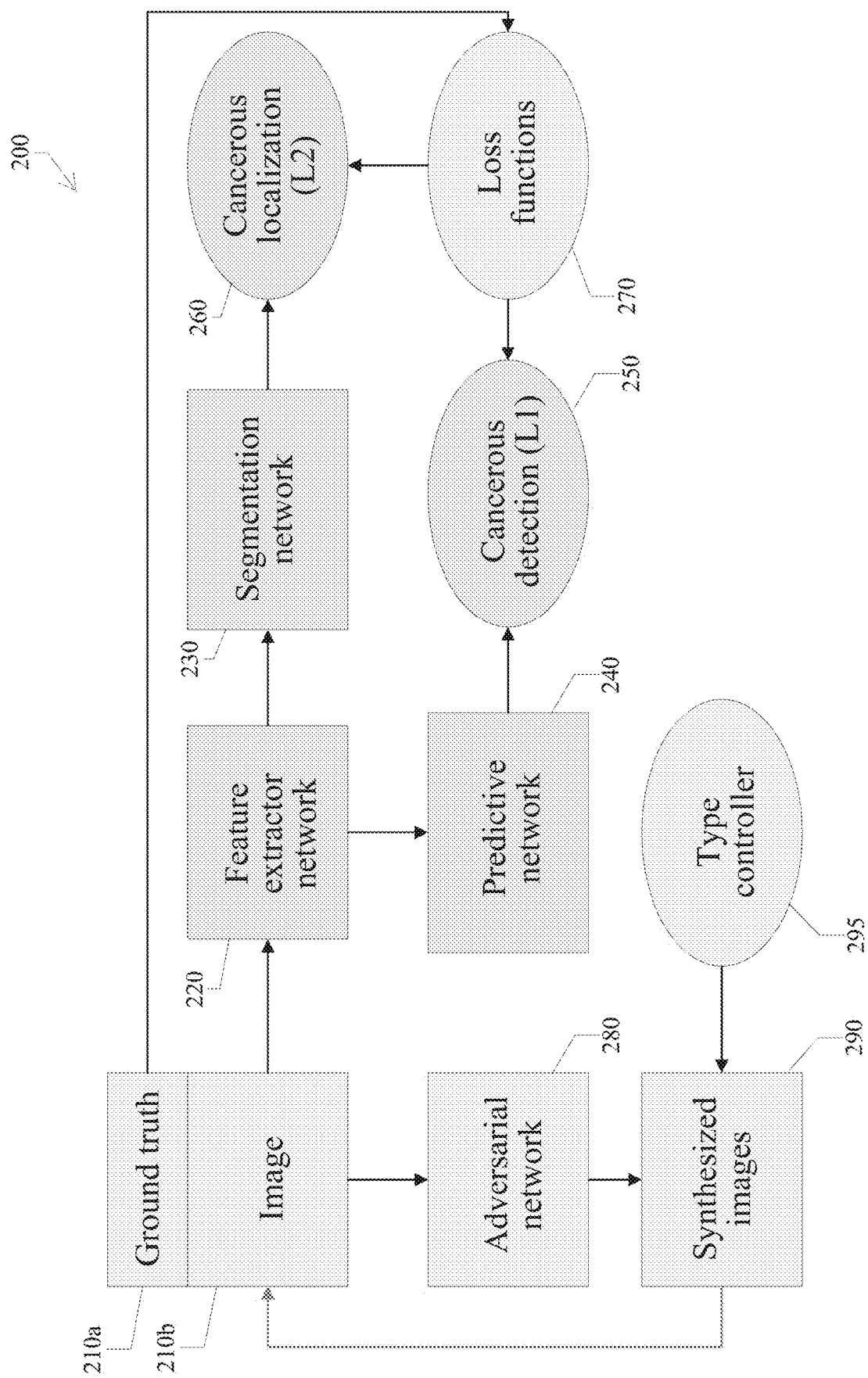
FIG. 2 is a block diagram illustrating a training phase of the AI.SKOPY system.

As is known, neural networks can provide image recognition functionality once trained with a data set. Referring to FIG. 2, a training phase 200 of the system 120 is described. The framework contains three major parts:
1. Level-1 prediction network (L1PN): to detect whether the image is cancerous or not. Also, the system provides a confidence parameter of the detection result.
2. Level-2 prediction network (L2PN): to label the location of the cancer region(s) in the image (if any).
3. Adversarial network (AN): used to generate the synthesized M-NBI images with or without cancerous regions.

Figure 3:
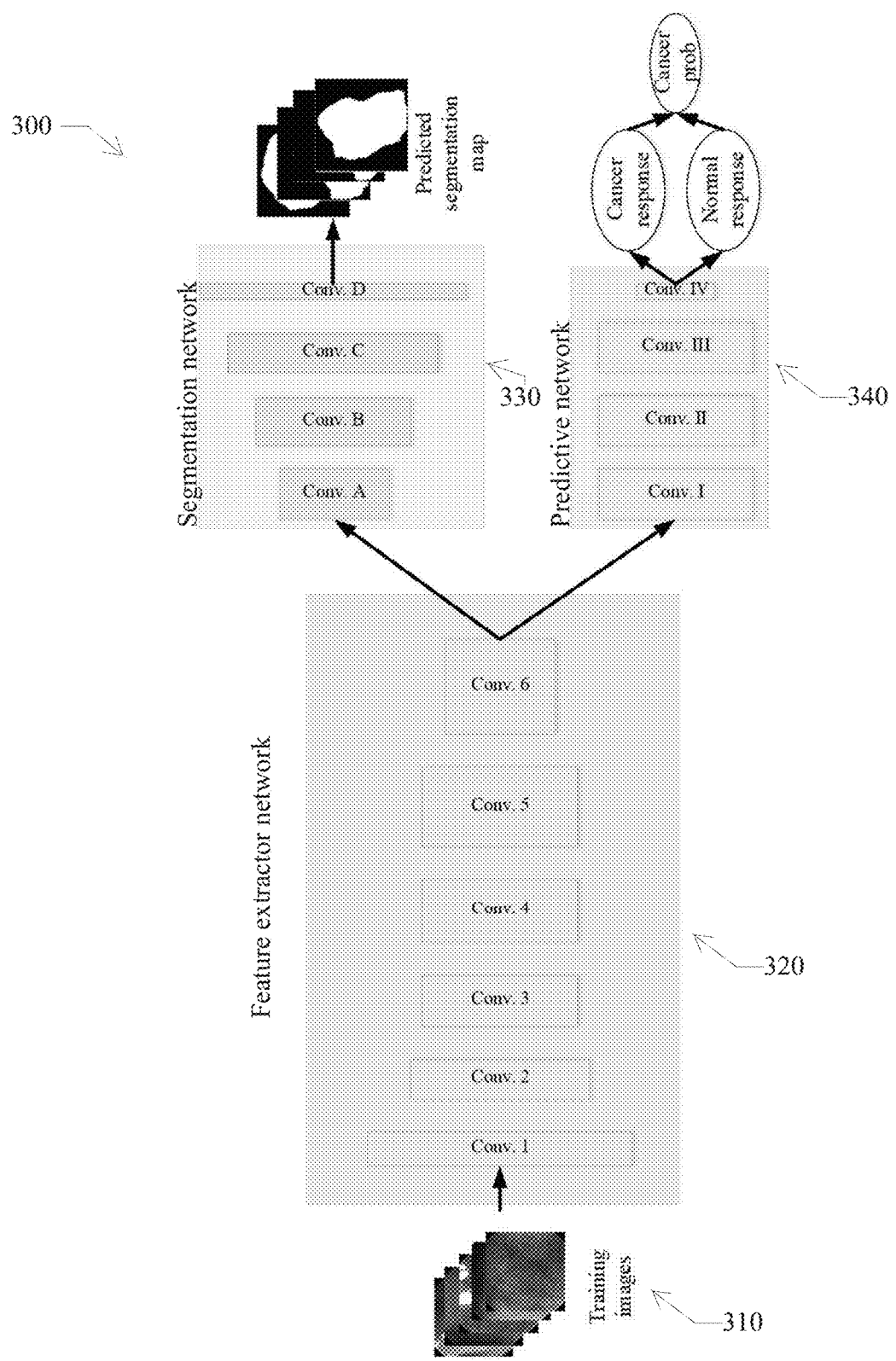
FIG. 3 is a block diagram illustrating network architectures of the feature extractor, segmentation, and predictive nets.

The details of the training phase of the system 120 are described as follows. The training images with their labels 210b are used to train four networks: a feature extractor network 220, a segmentation network 230, a predictive network 240 and an adversarial network 280. First, the training images 210b are input to the feature extractor net 220 (for which an architecture/structure is shown in FIG. 3) to extract two hundred fifty-six (256) feature maps, in certain embodiments. Each feature map is input to the predictive network 240 to generate two response values ranged in 0-1. A first response value indicates probability of the cancerous $P^+$ and a second response value indicates probability of the noncancerous P⁻ in an image. The cancer probability P of an image is determined by:

$P=P^+(P^+ +P^-)$.

The networks 220 and 240 can be updated by comparing the predicted labels 250 by predictive net 240 with ground truths 210a (labelled by physicians). This branch is referred to as L1PN (network 220 to network 240).

Referring to FIG. 3, the network architecture 300 is depicted. A set of training images 310 are provided as input to a feature extractor network 320 that is constructed by six dense blocks [Ref1: Huang, Gao, et al. "Densely connected convolutional networks", CVPR, Vol. 1, No. 2, 2017, p. 3]. In Ref1, a densely connected convolutional network (DenseNet) is proposed that uses direct connections from any layer to all subsequent layers. Consequently, the $\ell^{th}$ layer receives the feature-maps of all preceding layers, $x_0, \ldots, x_{\ell-1}$, as input: $x_\ell = H_\ell([x_0, x_1, \ldots, x_{\ell-1}])$, where $[x_0, x_1, \ldots, x_{\ell-1}]$ refers to the concatenation of the feature-maps produced in layers $0, \ldots, \ell-1$. For ease of implementation, the multiple inputs of $H_\ell(\cdot)$ in the equation of this paragraph can be concatenated into a single tensor. An image $x_0$ is passed through a convolutional network having L layers, each of which implements a non-linear transformation $H_\ell(\cdot)$, where $\ell$ indexes the layer. $H_\ell(\cdot)$ can be a composite function of operations such as batch normalization (BN), rectified linear units (ReLU), pooling, or convolution (Conv). The output of the $\ell^{th}$ layer is identified as $x_\ell$.

A DenseNet is a built by several dense blocks. As mentioned in Ref1 at page 4, Table 1, the typical DenseNet is at least 58 dense blocks. In this development, only six dense blocks are adopted in the feature extractor network to have a more efficient performance. One task of this system is to identify whether the image is cancerous or not. Compared to the task described in Ref1, the task of this system is different and, therefore, this system does not need as many dense blocks.

A segmentation network 330 receives the output of the feature extractor network 320. The segmentation network 330 is inspired by the fully convolutional network proposed in [Ref2: Long, Jonathan, Evan Shelhamer, and Trevor Darrell, "Fully convolutional networks for semantic segmentation", Proceedings of the IEEE conference on Computer Vision and Pattern Recognition, 2015], the convolutional layer is used on the last layer replaced with a densely connected layer [Ref2 p. 3, FIG. 2]. A difference between the segmentation network and fully convolutional networks (FCN) is that the feature extractor network is used as the input to segmentation network, whereas the FCN uses AlexNet, Vgg16, or GoogleNet network architecture as the input to the final convolutional layer [Ref2 p. 5, Table 1]. Compared to AlexNet, the DenseNet can provide more meaningful feature representation and also provide higher performance in the segmentation result.

Referring back to FIG. 2, the two hundred fifty-six (256) feature maps are regarded as the input of the segmentation network 230, (where the architecture can be referred to FIG. 3). Then, the segmentation network is used to up-sample these features to high-resolution segmentation results. Again, the feature extractor network 220 and segmentation network 230 can be updated by comparing the predicted segmentation map 260 with the ground truths 210a. This branch is referred to as L2PN using network 220 to network 230. The details of a training phase of L1PN and L2PN are described below.

In the training phase, the original training images are used to train both L1PN and L2PN based on the predefined loss functions. Meanwhile, the training images are randomly replaced with the generated images from AN by a type controller (TC) 295. The TC is a scalar that is used to determine whether the generated image containing cancer region(s) or not. In this case, TC is either a 0 or 1. A TC=1 means the generated images must contain a cancer region. The training phase of AN is described later. This step is used to augment the diversity of the training sample and it is also a key to train an effective model for a small-scale training set. Afterward, the feature extractor 220 and predictive nets 240 are trained. The optimal weights in the feature extractor network and the predictive network are saved after training processing. Then, all weights in the predictive network and the weights of Convolution (Conv.) 1 to Conv. 5 in the feature extractor network 220 are fixed. Meanwhile, the weights in the segmentation network 230 and the weights of Conv. 6 in the feature extractor network 220 are learned by the loss function used in L2PN. Finally, all learned weights are saved as a model file. On any testing task, the system pre-loads the model file to restore all optimal weights in the feature extractor, segmentation, and predictive networks and feeds an M-NBI image to the AI.SKOPY system 120 to obtain the L1 and L2 results, respectively.

Training Phase of L1PN

The loss function for L1PN can be defined as any label-wise loss function. In certain embodiments, cross-entropy is used as follows:

$$E_L = -\sum_{i=1}^{N} w_i p_i \log q_i$$

where $p_i$ is a predicted label and is $q_i$ the L1 ground truth (1 indicates a cancerous image and 0 indicates a noncancerous image). Note that the L1 output and its ground truth is a scalar value. In this manner, the loss function is used to measure the difference between the predicted result and its ground truth (right answer), which can be used to infer the gradient information. The gradient, obtained by the loss function, can be used to update the weights in the feature extraction network 220 and the predictive network 240 (FIG. 2). The updating manner is based on the standard stochastic gradient descent (SGD) [Ref4: Kingma, D. P., & Ba, J. L. (2015), Adam: A Method for Stochastic Optimization, International Conference on Learning Representations, 1-13].

Training Phase of L2PN

The loss function for L2PN can be defined as any reconstruction loss function. In certain embodiments, L2 norm distance is used to measure the distance between the predicted segmentation map and its L2 ground truth as follows:

$$E_R = \sum_{i=1}^{N} \|p_i - q_i\|^2.$$

Note that the predicted result and its ground truth is an image type. In L2PN, similarly, the loss function 270 (FIG. 2) is used to update the weights of the feature extraction network and segmentation network by standard SGD [Ref4] as well. Finally, the weights in blocks 220, 230 and 240 of FIG. 2 can be updated by the above two loss functions.

In addition, an effective deep learning neural network, i.e., a neural network with multiple levels, could be difficult to train with a small-scale data set, especially in L2PN in which the number of training images is relatively low. Therefore, a unique data augmentation method has been designed and developed to overcome this shortcoming as follows.

Content-Aware Data Augmentation of Training Phase of L2PN

Figure 4:
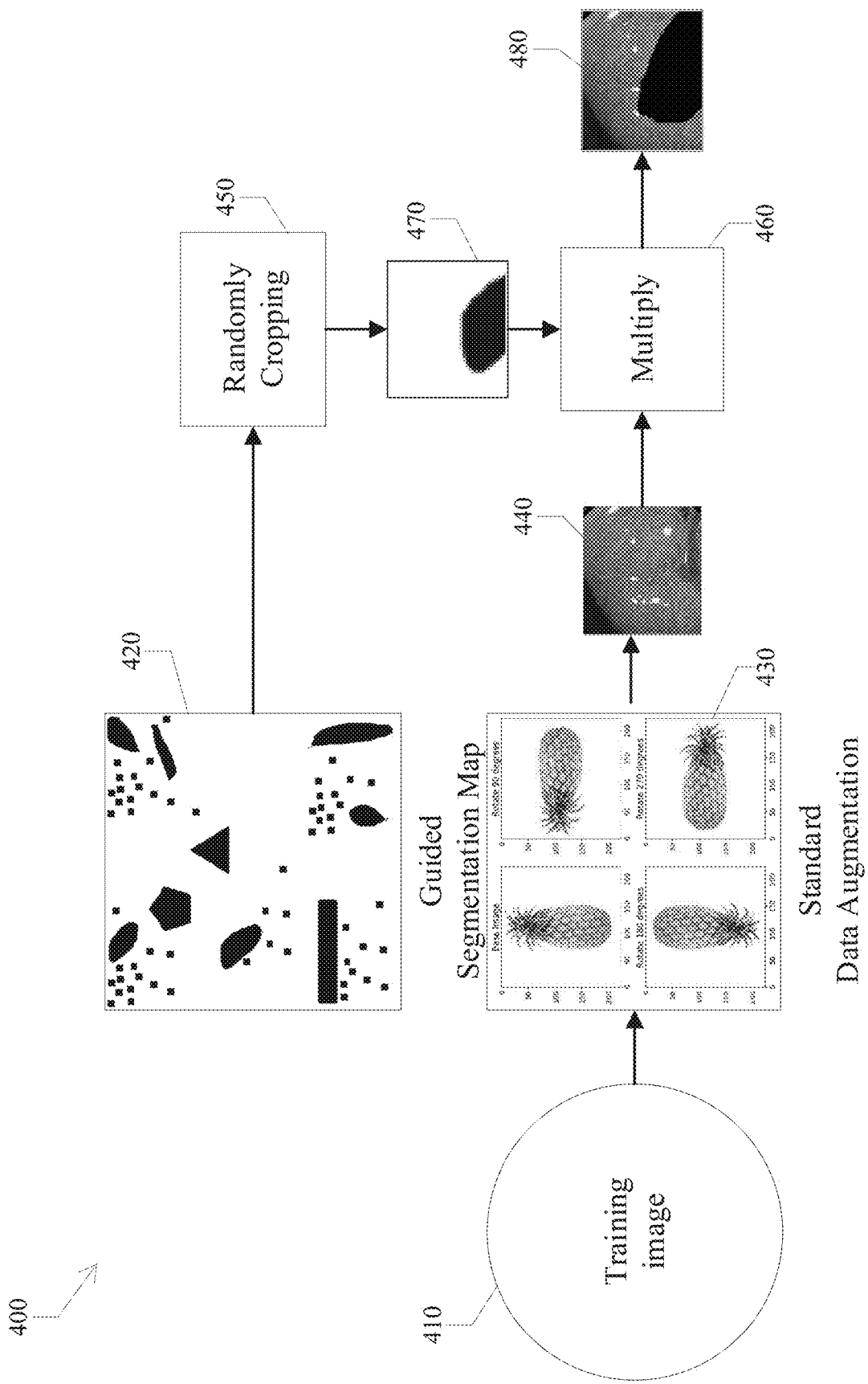
FIG. 4 is a block diagram illustrating a data augmentation method for a training phase of an adversarial network (AN).

In a Content-aware Data Augmentation (CDA) method 400, any training image 410 can be processed by several steps as described in FIG. 4. First, a standard data augmentation 430 is performed on the training image 410 sized as 224×224, including a vertical flip, a horizontal flip, and 90, 180, and 270 degree rotations. This yields six possible images including the original one. Then a guided segmentation map 420 is developed with a resolution of 2048×2048. A random crop operation 450 is used on this guided segmentation map 420 to obtain a sub-map 470 sized as 224×224. Then, the image 470 and image 440 are multiplied 460 to obtain a processed training image 480. In this manner, each training image is randomly corrupted in some parts according to the guided segmentation map 420 and enlarges the size of the training set. In some embodiments, the guided segmentation map can be arbitrarily modified.

Training Phase of AN

The basic idea of the generative adversarial network (GAN) is a min-max optimization [Ref3: Goodfellow, Ian, et al., "Generative adversarial nets", Advances in neural information processing systems, 2014]. In an example shown in FIG. 5, a generator 530 and 560 aims to synthesize an image from input that can fool a discriminator 540 and 570. The main task of the discriminator is to check whether the input image is synthesized or not. If the generator is a winner, the generated image can be regarded as a realism image. The network architectures of the generator 560 and discriminator 570 are illustrated in FIG. 6 as generator 610 and discriminator 620. A traditional GAN is used to randomly generate arbitrary realism images from random noise [Ref. 3]. In this development, there is a need to control the synthesized images with or without cancer region(s). However, the conventional GAN cannot be used for this task because the conventional GAN cannot specify the type of synthesized images. The new AN of this development can be used to resolve this issue, as shown in FIG. 5.

Figure 5:
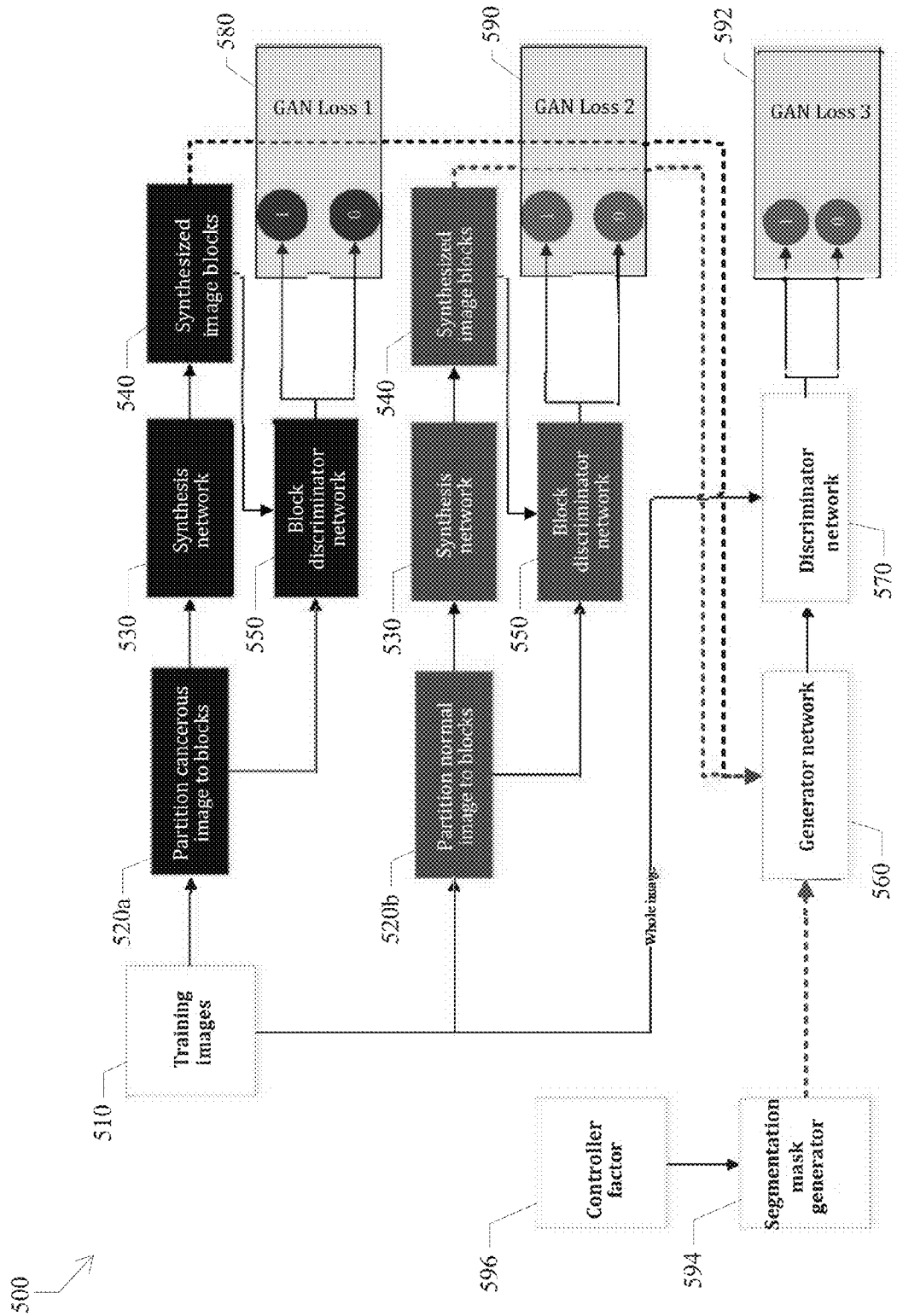
FIG. 5 is a block diagram illustrating a training phase of the AN.
Figure 6:
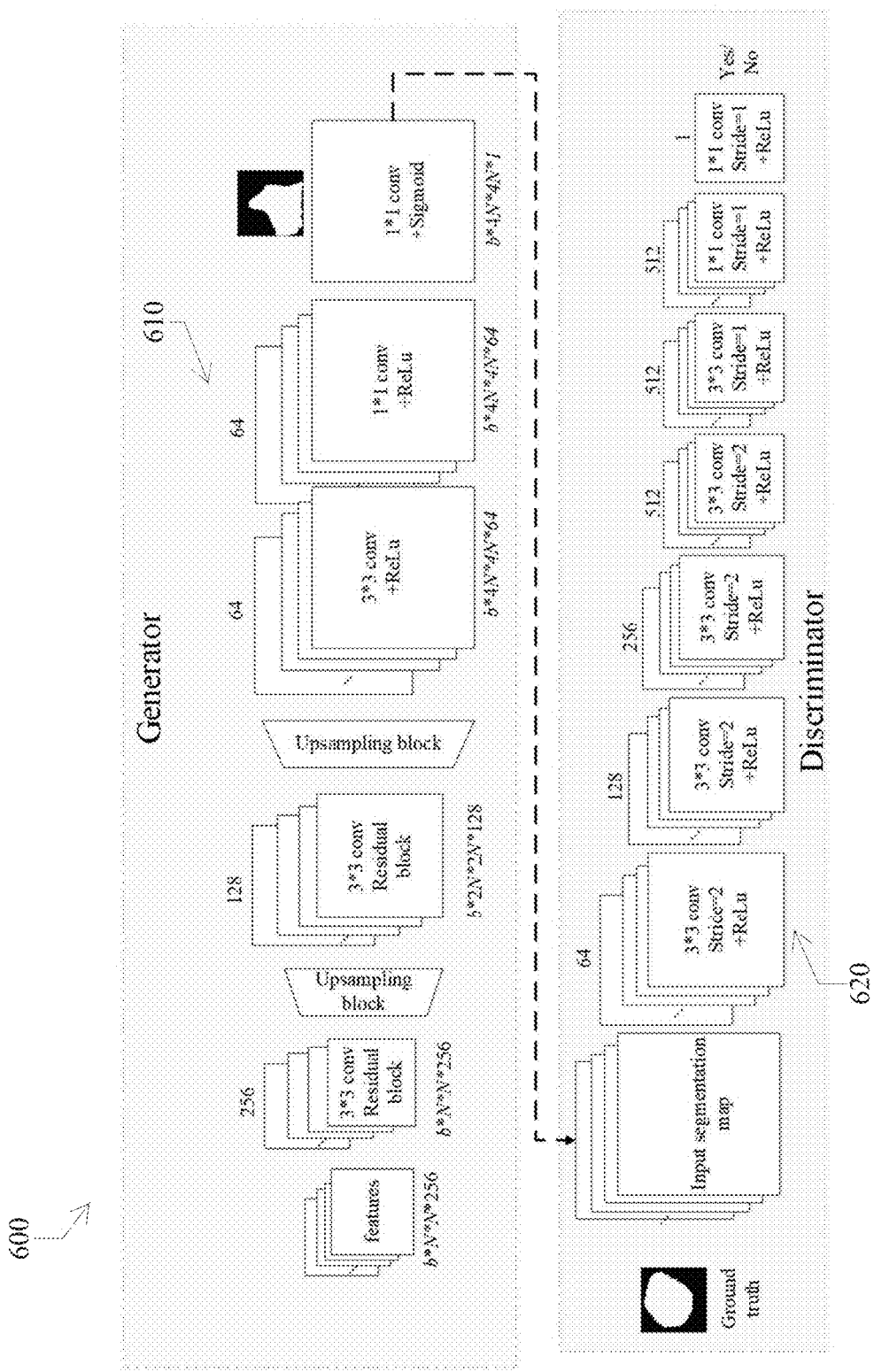
FIG. 6 is a block diagram illustrating network architectures of the generator and discriminator networks.

In the AN shown in FIG. 5, there are three GANs (generative adversarial networks) for a specified image synthesis task. The first and second GANs are used to generate cancerous image blocks or normal image blocks. Toward this end, the training images are partitioned into cancerous and normal image blocks, respectively. Then, the cancerous image blocks 520a are used to train the first GAN (called cancerous GAN, CGAN, 530-black and 550-black) and update the parameters of the first GAN by following standard GAN loss function:

$$J(G1) = \min_{G1} \max_{D1} V(D1, G1) = E_{x \sim p_x(x)}[\log D1(x)] + E_{z \sim p_z(z)}[\log(1 - D(G1(z)))]$$

where D1 (550-black) is a discriminator and G1 (530-black) is the generator.

Similarly, we can train a GAN model for normal image blocks in the same way (called normal GAN, NGAN), as follows:

$$J(G2) = \min_{G2} \max_{D2} V(D2, G2) = E_{x \sim p_x(x)}[\log D2(x)] + E_{z \sim p_z(z)}[\log(1 - D2(G2(z)))]$$

where D2 (550-brown) is a discriminator and G2 (530-brown) is the generator. Please note that the components in NGAN and CGAN can be the same as each other.

Once the models for CGAN and NGAN are trained, the generator network 560 is adapted to fuse the cancerous and normal image blocks according to the randomly generated segmenation map 594. The controller factor 596 is either a 0 or 1. The controller factor can be used as follows. When controller factor is a 1, the cancer region is randomly generated by an arbitrary shape and size in the segmentation map. When the controller factor is a 0, the segmentation map 594 will be a blank image (i.e., no cancer region). The synthesized images by the generator are sent to the discriminator network 570 to check whether the images are real or fake. Once the discriminator network 570 regards the synthesized image as real, the training process can be terminated. Finally, the final GAN (560 and 570) can be updated by:

$$J(G3) = \min_{G3} \max_{D3} V(D3, G3) = E_{x \sim p_x(x)}[\log D3(x)] + E_{z \sim p_z(z)}[\log(1 - D3(G3(z)))]$$

where D3 (570) is a discriminator and G3 (560) is the generator. In certain embodiments, the components in this GAN can be the same as with the NGAN and CGAN.

Testing Phase

Figure 7:
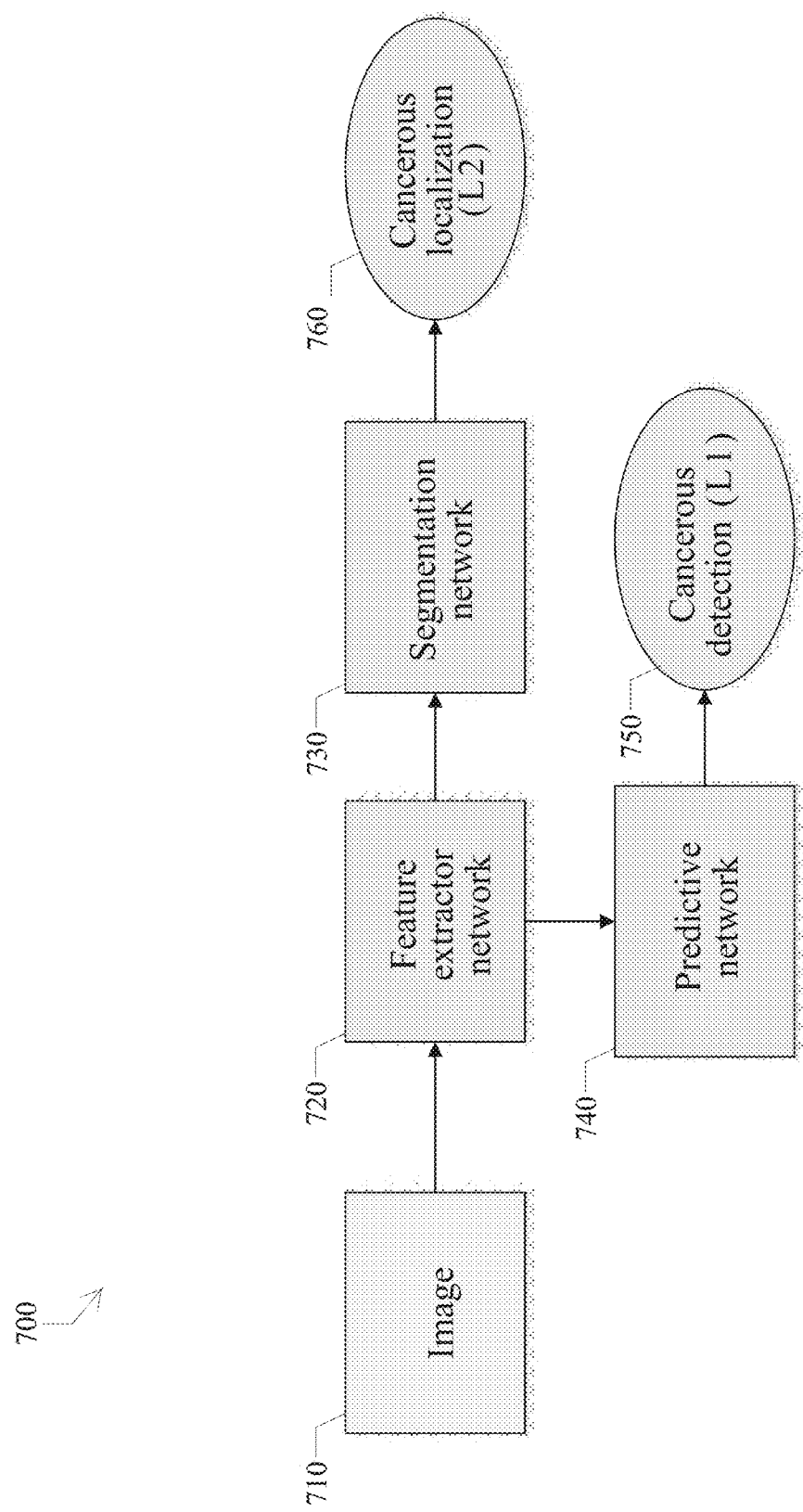
FIG. 7 is a block diagram illustrating a testing phase of both the Level-1 and Level-2 predictions.
Figure 8:
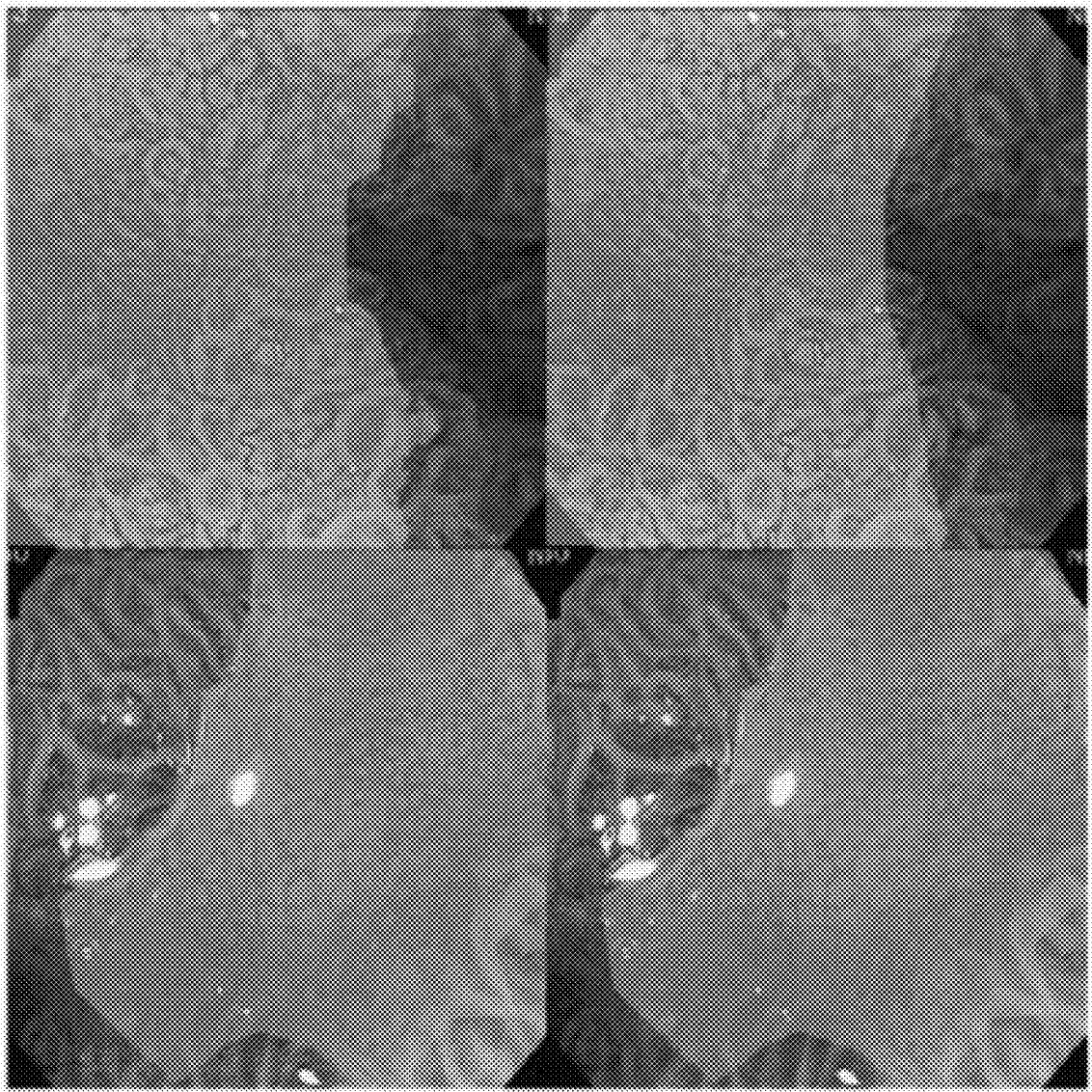
FIG. 8 is an image example of a Level-2 prediction network output identifying cancerous areas contrasted with physician annotated cancerous area output.
Figure 9:
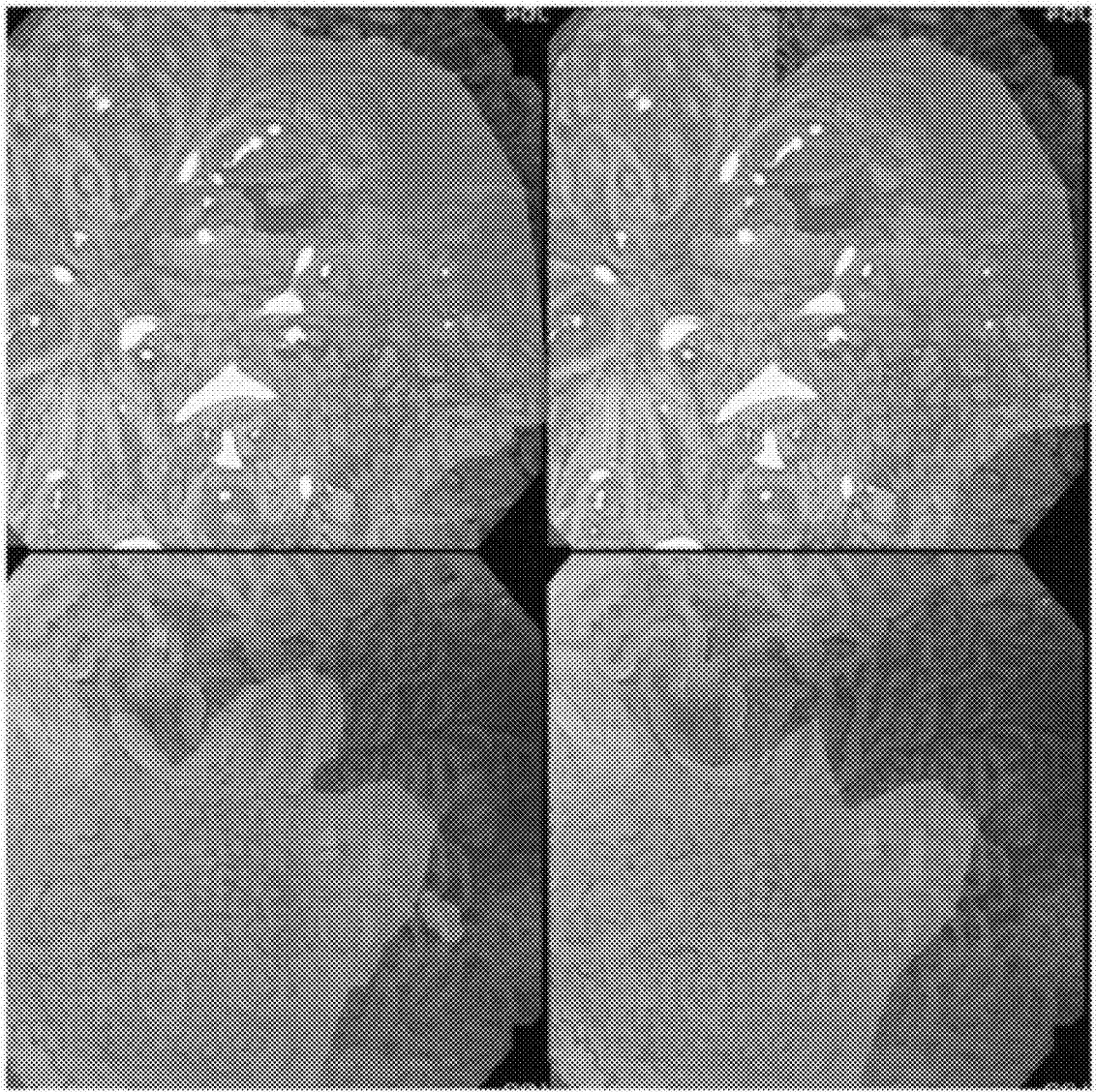
FIG. 9 is another image example of a Level-2 prediction network output identifying cancerous areas contrasted with physician annotated cancerous area output.
Figure 10:
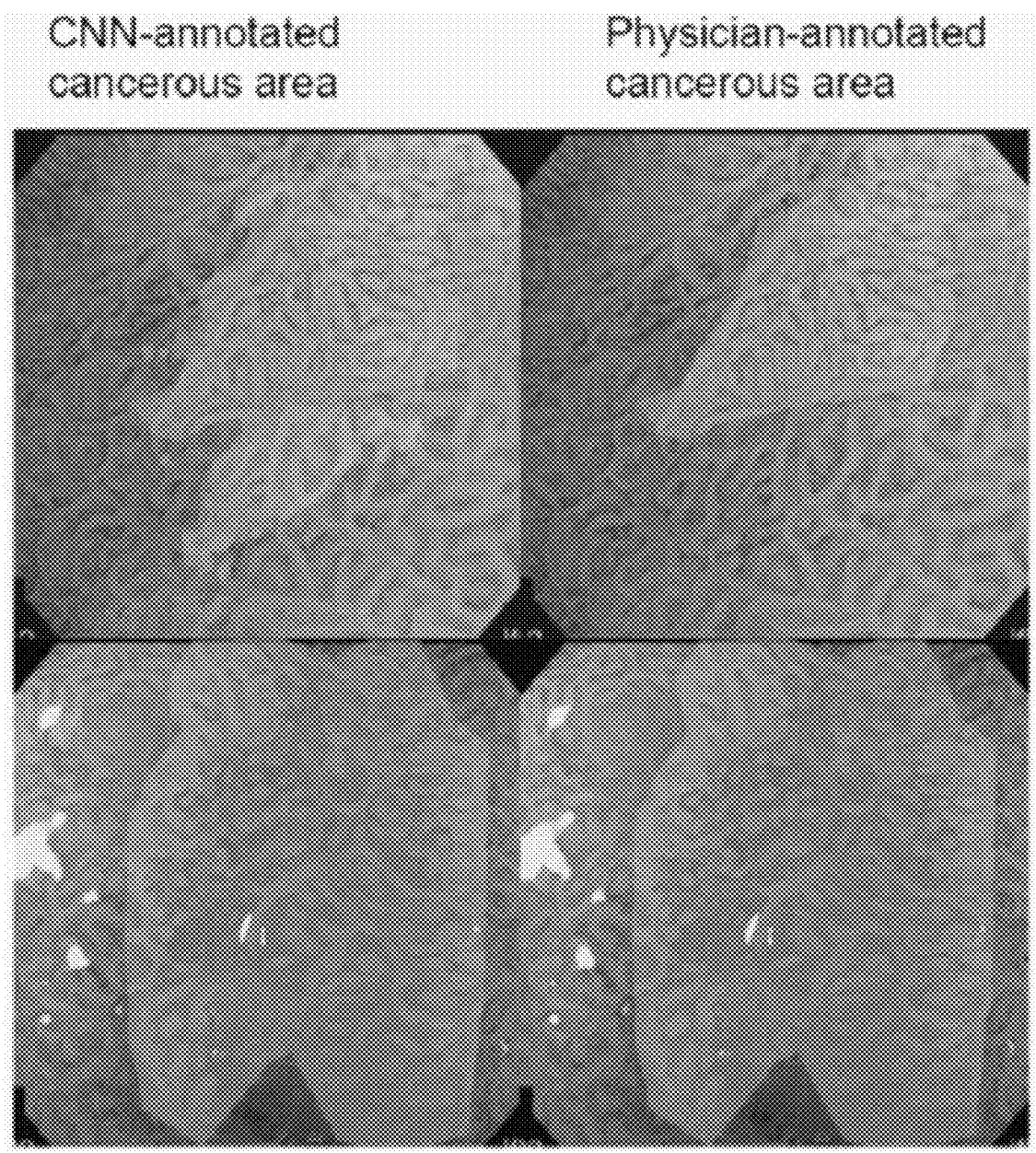
FIG. 10 is another image example of a Level-2 prediction network output identifying cancerous areas contrasted with physician annotated cancerous area output.
Figure 11:
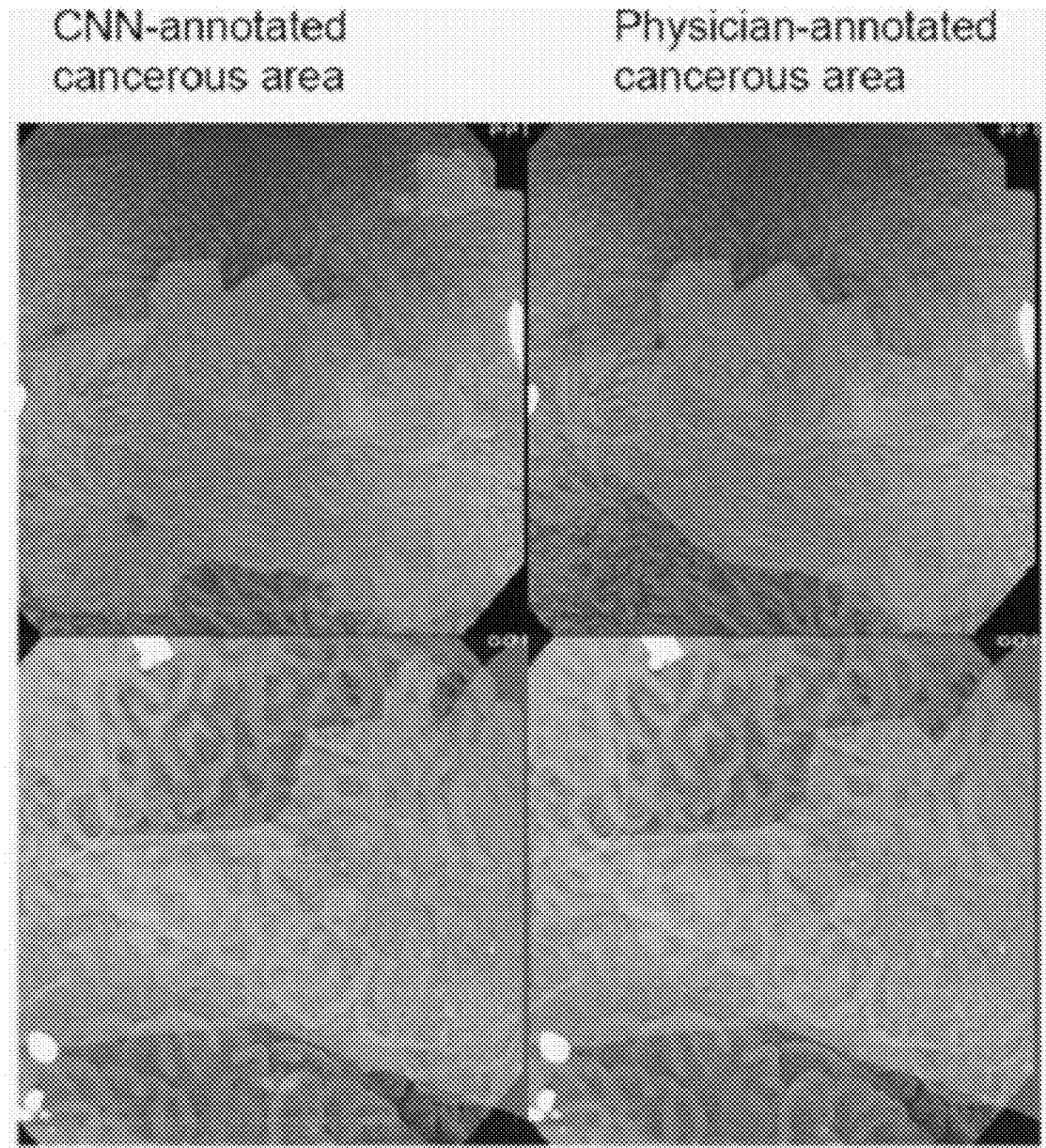
FIG. 11 is another image example of a Level-2 prediction network output identifying cancerous areas contrasted with physician annotated cancerous area output.
Figure 12:
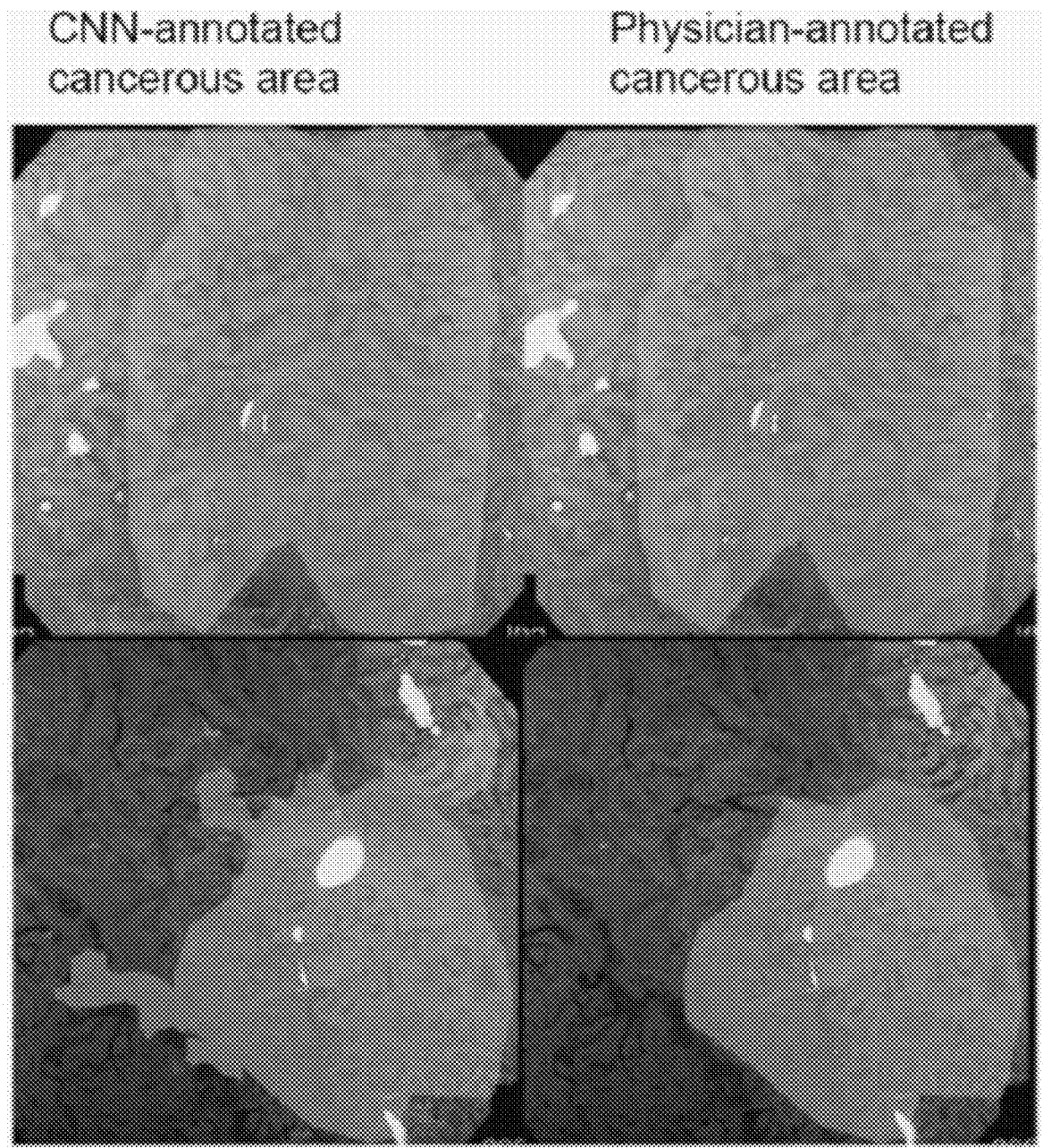
FIG. 12 is yet another image example of a Level-2 prediction network output identifying cancerous areas contrasted with physician annotated cancerous area output.

A testing phase configuration 700 for L1PN 750 and L2PN 760 can include images 710, a feature extractor 720, segmentation layers 730, and predictive layers 740, as shown in FIG. 7. The L1 and L2 predicted results of an M-NBI image can be obtained by passing through the image to the L1PN and L2PN.

Experiments

In a first set of experiments, there are three datasets totally: A (130 images), B (343 images) and C (video, 3000 frames). There are two testing sets: T1: 70 cancerous images and 60 normal images from dataset A and B; and T2: 30 cancerous images and 30 normal images from three datasets. The results are listed in the Table I. The runtime of an image is 10 ms. and the frame-rate is approximate to 70 frames per second (FPS) in a personal computer equipped with a Nvidia GPU Titan X. Table I shows the L1 performance results and Table II show the L2 performance results.

TABLE I

The L1 performance result.

| | Precision | Recall | Specificity | Accuracy | F-measure | Youden index |
|---|---|---|---|---|---|---|
| Test Set I | 0.9155 | 0.9286 | 0.9000 | 0.9154 | 0.9220 | 1.8155 |
| Test Set II | 0.9655 | 0.9333 | 0.9667 | 0.9500 | 0.9492 | 1.9322 |

TABLE II

The L2 performance result.

| | Precision | Recall |
|---|---|---|
| Test Set I | 0.9301 | 0.9107 |
| Test Set II | 0.9168 | 0.8845 |

In a second set of experiments, there are three datasets for L1 testing: A (130 images), B (343 images) and C (video frames, 5565 images). The test set includes 30 positive and 30 negative images. Table III shows the L1 performance results. For L2 testing, there are two datasets: A (130 images) and B (343 images). The test set includes 30 positive and 30 negative images. Table IV shows the L2 performance results.

L1 Output—Improved Results
3 datasets: video frames (5565 images), set 2 (343 images), set 1 (130 images)
Training set: 5,978 images
Test set: 30 positive, 30 negative

TABLE III

L1 improved performance results

| | | Precision | Recall | Specificity | Accuracy | F-measure | Youden Index |
|---|---|---|---|---|---|---|---|
| Test results | 2017Q4 version | 0.8000 | 0.7742 | 0.7931 | 0.7833 | 0.7869 | 1.5931 |
| | 2018Q4 version | 0.8649 | 0.9143 | 0.8333 | 0.8769 | 0.8889 | 1.6982 |

L2 Output in pixel-wise accuracy—Improved Results 2 datasets: set 2 (343 images), set 1 (130 images)

Training set: 473 images

Test set: 30 positive, 30 negative

TABLE IV

L2 improved performance results

| | | Accuracy | MAE |
|---|---|---|---|
| 2017Q4 Version | Test set | 0.8103 | 1.879 |
| 2018Q4 Version | | 0.9104 | 1.093 |

Run time: 10 ms in averaging
Maximum run-time: 67 ms on Personal Computer with Titan X
Mean run-time: 26.5 ms on Personal Computer with Titan X
Maximum run-time: 556 ms on Nvidia TX2
Mean run-time: 130 ms on Nvidia TX2
Maximum run-time: 88 ms on Laptop with GTX 1050 2G
Mean run-time: 39 ms on Laptop with GTX 1050 2G In a recent set of experiments at a hospital, one configuration tested include a PC having an Intel i7-7700 processor with 16 GB DDR4 RAM, GTX 1080Ti 11 GB graphics card and 480 GB SSD. In certain embodiments, an HDMI to VGA converter was used to provide system resolution of 640×480. A first-version algorithm based on a modified AlexNet (six convolution layers only) and the FCN feature was used on this configuration to achieve a mean (FPS)=12.25.

Another configuration utilized the Nvidia Jetson TX2 Module, which includes a dual-core Nvidia Denver2 and a quad-core ARM Cortex-A57 as the CPU complex, a 256-core Pascal GPU, 8 GB LPDDR4 and a 32 GB eMMC. Jetson TX2 is a fast, most power-efficient embedded AI computing device. A second-version algorithm based on a modified AlexNet (six convolution layers only) and the FCN feature was used on this configuration to achieve a mean FPS=10.15. The second version algorithm differed from the first version in that python code optimization was performed to reduce execution complexity. A third version algorithm, utilizing the same Nvidia Jetson TX2 Module, is based on a stack of six dense blocks, the FCN feature and content-aware data augmentation. The mean FPS for this configuration is 8.1.

Alternative Embodiments

Alternatives to the embodiment described above are now described. In certain embodiments, the GAN can be replaced with any CNN that can be used to synthesize an image. In certain embodiments, any framework that can generate discriminative training samples may be treated as a similar work to the previous described embodiments.

Conclusion

Skilled technologists will understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Skilled technologists will further appreciate that the various illustrative logical blocks, modules, circuits, methods and algorithms described in connection with the examples disclosed herein may be implemented as electronic hardware, computer software, or combinations of both. To clearly illustrate this interchangeability of hardware and software, various illustrative components, blocks, modules, circuits, methods and algorithms have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the examples disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The methods or algorithms described in connection with the examples disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other suitable form of data storage medium now known or made available in the future. A storage medium may be connected to the processor such that the processor can read information from, and write information to, the storage medium. In the alternative, the storage medium may be integral to the processor. The processor and the storage medium may reside in an ASIC.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, rather than sequentially.

The previous description of the disclosed examples is provided to enable any person skilled in the art to make or use the present invention. Various modifications to these examples will be readily apparent to those skilled in the art, and the generic principles defined herein may be applied to other examples without departing from the spirit or scope of the invention. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope. Thus, the present invention is not intended to be limited to the examples shown herein but is to be accorded the widest scope consistent with the principles and novel features disclosed herein.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

What is claimed is:

1. A method of diagnosing gastrointestinal neoplasm or pathologies in an endoscopy system including an endoscopy system display for the display of an image enhanced endoscopy (IEE) image, the method comprising:
    randomly generating training image samples with or without cancer region(s) by an adversarial network (AN), comprising:
        collecting endoscopic training images (T1);
        partitioning the training images into training normal blocks and training cancerous blocks according to a corresponding segmentation map (S1);
        learning to automatically generate cancerous blocks using a cancerous generative adversarial network (CGAN) from the training cancerous blocks;
        learning to automatically generate normal IEE image blocks using a normal generative adversarial network (NGAN) from the training normal blocks;
        randomly generating segmentation maps (S2) comprising a black and white image based on the automatically generated cancerous blocks and the automatically generated normal IEE image blocks, wherein any white pixels indicate a cancerous region, and wherein the segmentation map can be black pixels only, which is indicative of no cancer;
        learning to automatically generate a realistic IEE image as a new training image sample (T2) using a generator network in the AN from the generated segmentation map;
    using a level 1 prediction network (L1PN) to learn a level 1 prediction result being a cancerous probability of an IEE image from the collected T1 and T2, wherein T2 is generated by the AN;
    using a level 2 prediction network (L2PN) to learn a level 2 prediction result being detected cancerous region(s) of an IEE image from the collected T1 and T2, wherein T2 is generated by the AN; and
        predicting the level 1 result and the level 2 result for an IEE image using the L1PN and the L2PN and without using the AN.

2. The method of claim 1, wherein the IEE images include at least one of magnified narrow-band imaging, endocytomicroscopy, i-SCAN, flexible spectral imaging color enhancement, blue laser imaging, and bright laser imaging.

3. The method of claim 1, wherein the segmentation map (Si) comprises a ground truth.

4. The method of claim 3, wherein the ground truth is labeled by a physician.

5. The method of claim 1, additionally comprising generating additional training images based on the collected endoscopic training images, the generating comprising:

rotating or flipping a collected endoscopic training image to create one or more augmented training images;

providing a guided segmentation map having a resolution greater than the collected endoscopic training images;

randomly cropping the guided segmentation map to obtain a sub-map having a resolution equal to the resolution of the collected endoscopic training images; and multiplying the sub-map with each of the augmented training images so as to produce additional training images.

6. The method of claim 1, wherein the detected cancerous region(s) of the level 2 prediction result are at a pixel level of resolution.

7. A system for diagnosing gastrointestinal neoplasm or pathologies in an endoscopy system including an endoscopy system display for the display of an image enhanced endoscopy (IEE) image, the system comprising:

means for randomly generating training image samples with or without cancer region(s) by an adversarial network (AN), comprising:

means for collecting endoscopic training images (T1);

means for partitioning the training images into training normal blocks and training cancerous blocks according to a corresponding segmentation map (Si);

means for learning to automatically generate cancerous blocks using a cancerous generative adversarial network (CGAN) from the training cancerous blocks;

means for learning to automatically generate normal IEE image blocks using a normal generative adversarial network (NGAN) from the training normal blocks;

means for randomly generating segmentation maps (S2) comprising a black and white image based on the automatically generated cancerous blocks and the automatically generated normal IEE image blocks, wherein any white pixels indicate a cancerous region, and wherein the segmentation map can be black pixels only, which is indicative of no cancer;

means for learning to automatically generate a realistic IEE image as a new training image sample (T2) using a generator network in the AN from the generated segmentation map;

means for using a level 1 prediction network (L1PN) to learn a level 1 prediction result being a cancerous probability of an IEE image from the collected T1 and T2, wherein T2 is generated by the AN;

means for using a level 2 prediction network (L2PN) to learn a level 2 prediction result being detected cancerous region(s) of an IEE image from the collected T1 and T2, wherein T2 is generated by the AN; and means for predicting the level 1 result and the level 2 result for an IEE image using the L1PN and the L2PN and without using the AN.

8. The system of claim 7, wherein the IEE images include at least one of magnified narrow-band imaging, endocytomicroscopy, i-SCAN, flexible spectral imaging color enhancement, blue laser imaging, and bright laser imaging.

9. The system of claim 7, wherein the segmentation map (Si) comprises a ground truth.

10. The system of claim 9, wherein the ground truth is labeled by a physician.

11. The system of claim 7, additionally comprising means for generating additional training images based on the collected endoscopic training images, the means for generating comprising:

means for rotating or flipping a collected endoscopic training image to create one or more augmented training images;

means for providing a guided segmentation map having a resolution greater than the collected endoscopic training images;

means for randomly cropping the guided segmentation map to obtain a sub-map having a resolution equal to the resolution of the collected endoscopic training images; and means for multiplying the sub-map with each of the augmented training images so as to produce additional training images.

12. The system of claim 7, wherein the detected cancerous region(s) of the level 2 prediction result are at a pixel level of resolution.

13. A method of randomly generating training image samples with or without cancer region(s) by an adversarial network (AN), in an endoscopy system for diagnosing gastrointestinal neoplasm or pathologies including an endoscopy system display for the display of an image enhanced endoscopy (IEE) image, the method comprising:

providing endoscopic training images (T1);

partitioning the training images into training normal blocks and training cancerous blocks according to a corresponding segmentation map (S1);

learning to automatically generate cancerous image blocks using a cancerous generative adversarial network (CGAN) from the training cancerous blocks;

learning to automatically generate normal image blocks using a normal generative adversarial network (NGAN) from the training normal blocks;

randomly generating a segmentation map (S2) comprising an image based on the automatically generated cancerous image blocks and the automatically generated normal image blocks; and learning to automatically generate a realistic IEE image as a new training image sample (T2) using a generator network in the AN from the generated segmentation map.

14. The method of claim 13, wherein any white pixels indicate a cancerous region in the segmentation map, and wherein the segmentation map can be black pixels only, which is indicative of no cancer.

15. A method of diagnosing gastrointestinal neoplasm or pathologies in an endoscopy system including an endoscopy system display for the display of an image enhanced endoscopy (IEE) image, the method comprising:

using a level 1 prediction network (L1PN) comprising feature extraction followed by segmentation to learn a level 1 prediction result being a cancerous probability of an IEE image from collected training images;

using a level 2 prediction network (L2PN) comprising feature extraction feeding a predictive network to learn a level 2 prediction result being detected cancerous region(s) of an IEE image from the collected training images; and predicting the level 1 result and the level 2 result for an IEE image using the L1PN and the L2PN.

* * * * *

UNITED STATES PATENT AND TRADEMARK OFFICE
CERTIFICATE OF CORRECTION

PATENT NO. : 11,011,275 B2
APPLICATION NO. : 16/273016
DATED : May 18, 2021
INVENTOR(S) : Chih-Chung Hsu It is certified that error appears in the above-identified patent and that said Letters Patent is hereby corrected as shown below:

In the Specification

In Column 9, Line 3, delete "$P=P^+(P^++P^-)$" and insert --$P=P^+/(P^++P^-)$--.

In the Claims

In Column 16, Claim 3, Line 62, delete "Si" and insert --S1--.

In Column 17, Claim 7, Line 25 (Approx.), delete "Si" and insert --S1--.

In Column 17, Claim 9, Line 62, delete "Si" and insert --S1--.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*